(12) United States Patent
Hong et al.

(10) Patent No.: US 6,458,934 B1
(45) Date of Patent: Oct. 1, 2002

(54) HUMANIZED ANTIBODY SPECIFIC FOR HUMAN 4-1BB

(75) Inventors: Hyo Jeong Hong; Sung Sup Park, both of Taejon; Young Jun Kang, Daejon; Chang-Yuil Kang, Seoul; Sung Kwan Yoon, Taejon, all of (KR)

(73) Assignee: LG Chemical Limited, Seoul (KR)

( * ) Notice: Subject to any disclaimer, the term of this patent is extended or adjusted under 35 U.S.C. 154(b) by 0 days.

(21) Appl. No.: 09/438,954

(22) Filed: Nov. 12, 1999

(30) Foreign Application Priority Data

Nov. 17, 1998 (KR) .............................. 98-19177
May 11, 1999 (KR) ........................... 99-16750

(51) Int. Cl.[7] ........................ C07K 16/18; C07K 16/28
(52) U.S. Cl. ................. 530/387.3; 530/387.1; 530/387.5; 530/388.1; 530/388.2; 530/388.22; 530/388.7; 530/388.73; 530/388.75
(58) Field of Search ............... 530/387.3, 387.1, 530/388.1, 388.22, 388.7, 388.73, 388.75, 350, 388.2; 424/130.1, 133.1, 137.1, 141.1, 143.1, 144.1, 152.1, 153.1, 154.1

(56) References Cited

U.S. PATENT DOCUMENTS 5,530,101 A * 6/1996 Queen et al.
5,928,893 A * 7/1999 Kang et al.
6,037,454 A * 3/2000 Jardieu et al.

OTHER PUBLICATIONS

Michel et al. Eur. J. Immunol. 1998; 28:290–295.*
Lee et al., Mol. Cells, 6(2):161–168, 1996.*
Bendig, M.M., Methods: A Comparison to Meth. Enzy. 8:83–93. 1995.*
Kingsley et al., Immunology Today 17(1):9–12, 1996.*

* cited by examiner

Primary Examiner—Phillip Gambel
Assistant Examiner—Jessica H. Roark
(74) Attorney, Agent, or Firm—Birch Stewart Kolasch & Birch LLP

(57) ABSTRACT

The present invention is directed to humanized antibodies that specifically bind the protein 4-1BB. The antibodies can be made by grafting of the complementarity determining regions (CDR's) of mouse monoclonal antibody to human 4-1BB to the remaining portions of a human antibody and by making further amino acid replacements. In addition, a pharmaceutical composition that includes the humanized antibody can be made and can be used to treat autoimmune diseases to suppress an immune response. The humanized antibody of the invention has high affinity for human 4-1BB, and exhibits sequence similarity to human antibody. As a result, the pharmaceutical composition of the present invention can be used to treat autoimmune disease and act as an immunosuppressant in humans without much side-effect.

4 Claims, 12 Drawing Sheets

```
kappa light chain
4B4      DIVMTQSQATQSVTPGDRVSLSC RASQTISDYLH WYQQKSHESPRLLIK
X82934   DVVMTQSPATLSVSPGERATLSC RASQSVSSYLA WYQQKPGQAPRLLIY
Hz4B4-1  DIVMTQSPATQSVSPGERVTLSC RASQTISDYLH WYQQKPGQSPRLLIK
Hz4B4-2  ---------P-L-L--------- ----S----- ---------------

4B4      YASQSIS GIPSRFSGSGSGSDFTLSINSVEPEDVGVYYC QDGHSFPPT FGGGTKLEIK
X82934   DASRRAT GIPARFSGSGSGTDFTLTISSLEPEDFAVYYC QRSNWPPLT FGGGTKVEIK
Hz4B4-1  YASQSIS GIPSRFSGSGSGSDFTLTISSVEPEDFGVYYC QDGHSFPPT FGGGTKLEIK
Hz4B4-2  ------- -----------A------T---------- --A------ ------V--- heavy chain
4B4      QVQLQQPGAELVKPGASVKLSCKASGYTFS SYWMH WVKQRPGQVLEWIG EINPGNGHTNYNEKFKS
M17750   QVQLVQSGAEVKKPGASVKVSCKASGYTFT SYAMH WVRQAPGQRLEWMG WINAGNGNTKYSQKFQG
Hz4B4-1  QVQLVQSGAEVVKPGASVKLSCKASGYTFS SYWMH WVKQAPGQVLEWIG EINPGNGHTNYNEKFKS
Hz4B4-2  --------K------V---------- ---- ----- ---R----M-- ----SQ--QG 4B4      KATLTVDKSSSTAYMQLSSLTSEDSAVYYCAR SFTTARAFAY WGQGTLVTVSA
M17750   RVTITRDTSASTAYMELSSLRSEDTAVYYCAR GGYYGSGSNY WGEGTLVTVSS
Hz4B4-1  KATLTVDKSASTAYMELSSLRSEDTAVYYCAR SFTTARAFAY WGQGTLVTVSS
Hz4B4-2  RV-I---------------------------- ---------- -----------
```

HUMANIZED ANTIBODY SPECIFIC FOR HUMAN 4-1BB

FIELD OF THE INVENTION

The invention relates to humanized antibodies that specifically bind to 4-1BB receptor proteins, preferably to human 4-1BB receptor protein. The humanized antibodies can be used as diagnostic reagents or can be formulated into pharmaceutical compositions for administration to a patient.

BACKGROUND OF THE INVENTION

The immune system has tremendous diversity and because the repertoire of specificities expressed by the B- and T-cell populations is generated randomly, it is bound to include many which are specific for self components. Thus, the body must establish self-tolerance mechanisms to distinguish between self and non-self determinants so as to avoid autoreactivity. However, all mechanisms have a risk of breakdown. The self-recognition mechanisms are no exception, and a number of diseases have been identified in which there is autoimmunity due to copious production of autoantibodies and autoreactive T cells.

There are at least 30 diseases which are either caused by or related to autoimmunity. Examples of such diseases include rheumatoid arthritis, pemphigus vulgaris, glomerulonephritis, pernicious anemia, thyroiditis and systemic lupus erythematosus. In Korea, one person in one hundred suffers from rheumatoid arthritis.

The transplantation of tissues to replace diseased organs is now an important medical therapy. In most cases, adaptive immune responses to the grafted tissues are the major impediment to successful transplantation. When tissues containing nucleated cells are transplanted, T-cell responses to the highly polymorphic MHC (major histocompatibility complex) molecules almost always trigger a response against the grafted organ. Matching the MHC type of donor and recipient increases the success rate of grafts, but perfect matching is possible only when donor and recipient are related and, in these cases, genetic differences at other loci still trigger rejection.

The immune system may be manipulated or controlled to suppress unwanted immune responses in autoimmune disease and graft rejection. Currently, several different immunosuppressive agents have been used clinically. The examples are methotrexate, azathiopurine, cyclophosphamide, prednisone, cyclosporine A, FK506 (tacrolimus), anti-lymphocyte globulin (ALG) and anti-thymocyte globulin (ATG). Very recently, antibodies by virtue of their exquisite specificity have been utilized for the therapeutic inhibition of specific immune responses. The target molecules for these antibodies can be divided into two groups. The first group includes molecules that are expressed on the surface of lymphocytes, such as CD3, CD4, IL-2R, CDw52 and ICAM-1. The other groups are mainly cytokines such as TNF-α and IL-6. Some of the antibodies are effective and are being sold as pharmaceutical products.

However, the presently developed immunosuppressants have a common problem in that cells that are not related to immune response or normal cells are all affected by the drugs. This causes serious side effects that cannot be avoided. Therefore, an immunosuppressant is desired that is specific for activated immune cells, has excellent immunosuppressive activity, and has no adverse side effect.

Although murine monoclonal antibodies are extensively used as diagnostic agents, their utility as therapeutics has been proven in only a few cases. The limited application is attributed to three major reasons. First, the repeated administration of murine monoclonal antibodies to humans usually elicits human immune responses against these molecules. The human anti-mouse antibody (HAMA) responses are directed to two different domains. The responses against the variable region are so called anti-idiotype responses which could block the antigen binding activity of murine antibodies. The responses against the constant region represent anti-isotype responses, which block the effector function of antibodies. The HAMA responses not only block the functions of newly administered antibodies but also result in formation of immune complexes with the murine antibodies, which cause some side effects and could reduce the half life of the antibody. Second, the half-life of murine antibodies even in the absence of immune complex formation is much shorter than that of human antibodies in vivo. Third, the effector functions through the Fc region of murine antibodies are weak or non-existent compared to those of human antibodies. All of the factors described above reduce the efficacy of murine monoclonal antibodies and are common problems related to human immunotherapy based on xenogeneically derived monoclonal antibodies.

To overcome the intrinsic undesirable properties of murine monoclonal antibodies, recombinant murine antibodies engineered to incorporate regions of human antibodies, so called "humanized antibodies", have been developed. This alternative strategy was adopted as is was very difficult to generate human antibodies directed to human antigens, such as cell surface molecules, due to tolerance of the immune system against self-antigens. A humanized antibody contains complementarity determining region (CDR) regions and a few other amino acid of a murine antibody and the rest of the structure is derived from a human antibody.

SUMMARY OF THE INVENTION 4-1BB is expressed on the surface of activated T-cells as a type of accessory molecule (Kwon et al., *Proc. Natl. Acad. Sci. USA* 86:1963 (1989); Pollok et al., *J. Immunol.* 151:771 (1993)), and is a membrane protein related to tumor necrosis factor receptor (TNFR) (Malett et al., *Immunol. Today* 12:220 (1991)). 4-1BB has a molecular weight of 55 kDa, and is found as a homodimer. In addition, 4-1BB binds to the protein kinase $p56^{1ck}$ inside the cell. It has been suggested that 4-1BB mediates a signal transduction pathway from outside of the cell to inside (Kim et al., *J. Immunol.* 151:1255 (1993)).

A human 4-1BB gene was isolated from a CDNA library made from activated human peripheral T-cell mRNA (Goodwin et al., *Eur. J. Immunol.* 23:2631 (1993)). The amino acid sequence of human 4-1BB shows 60% homology to mouse 4-1BB (Kwon et al., *Proc. Natl. Acad. Sci. USA* 86:1963 (1989)), which indicates that the sequences are highly conserved. Analysis of the amino acid sequence of 4-1BB indicates that it belongs to the nerve growth factor superfamily, along with CD40, CD27, TNFR-I, TNFR-II, Fas, and CD30 (Alderson et al., *Eur. J. Immunol.* 24:2219 (1994). When a monoclonal antibody is bound to 4-1BB expressed on the surface of mouse T-cells, anti-CD3 T-cell activation is increased many fold (Pollok et al., *J. Immunol.* 150:771 (1993)).

4-1BB binds to a high affinity ligand (4-1BBL) expressed on several antigen-presenting cells such as macrophages and activated B cells (Pollok et al., *J. Immunol.* 150:771 (1993); Schwarz et al., *Blood* 85:1043 (1995)). The interaction of 4-1BB and its ligand provides a costimulatory signal leading to T cell activation and growth (Goodwin et al., *Eur. J. Immunol.* 23:2631 (1993); Alderson et al., *Eur. J. Immunol.* 24:2219 (1994); Hurtado et al., *J. Immunol.* 155:3360 (1995); Pollock et al., *Eur. J. Immunol.* 25:488 (1995); DeBenedette et al., *J. Exp. Med.* 181:985 (1995). These observations suggest an important role for 4-1BB in the regulation of T cell-mediated immune responses (Ignacio et al., *Nature Med.* 3:682 (1997)).

The inventors have previously constructed a hybridoma producing a mouse monoclonal antibody that is specific for human 4-1BB (h4-1BB) expressed on the surface of activated T-cells (Korean patent laid-open no. 96-37064). As a result of the search by the inventors for an immunosuppressant specific for activated T-lymphocytes and that also has no adverse side effect, the inventors have constructed a humanized monoclonal antibody from a mouse monoclonal antibody to 4-1BB that is expressed only in activated T-lymphocytes (Korean patent laid-open no. 96-37064). The humanized monoclonal antibody has high affinity for 4-1BB. Administering the humanized anti-4-1BB monoclonal antibody to non-human primates does not elicit an anti-antibody response. Rather, it elicits strong immunosuppressive activity.

One object of the present invention is to provide a humanized monoclonal antibody that specifically binds 4-1BB, especially human 4-1BB (h4-1BB) that has a high affinity for 4-1BB (h4-1BB). The humanized antibodies of the present invention have high affinity for human 4-1BB, and bear sequence similarity to human antibodies. Because the 4-1BB receptor protein that is specifically bound by the antibodies of the invention appears to be involved in activation of the immune response, the product can be used effectively to treat autoimmune diseases or it can be used as an immunosuppressant to prevent graft rejection, Because the antibodies of the present invention closely resemble human antibodies, they can be administered to a human patient without any negative side-effect, such as a human anti-mouse antibody response.

Another object of the present invention is to provide a pharmaceutical composition comprising the humanized anti-h4-1BB monoclonal antibody. The pharmaceutical composition is useful for treating autoimmune diseases or acting as an immunosuppressant to prevent graft rejection. As rheumatoid arthritis is thought to be caused by inappropriate activity of 4-1BB receptor, the composition is especially useful for treating rheumatoid arthritis.

Another object of the invention is to provide a diagnostic composition for diagnosis of immune dysfunctions related to over- or underactivity of 4-1BB receptor protein.

BRIEF DESCRIPTION OF THE DRAWINGS

FIG. 1—Amino acid sequence comparison of the variable region of heavy (VH) and light chain (VL) of the humanized anti-human 4-1BB antibodies, Hz4B4-1 (SEQ ID NO:2 and SEQ ID NO:1, respectively) and Hz4B4-2 (SEQ ID NO:4 and SEQ ID NO:3, respectively). These sequences are compared with the amino acid sequence of mouse monoclonal antibody 4B4-1-1 (SEQ ID NO:39 and SEQ ID NO:38, respectively), human antibody VH M17750 (SEQ ID NO:41), and human antibody VL X82934 (SEQ ID NO:40).

FIG. 2—Location of the primers used in PCR synthesis of the genes encoding VH and VL of humanized antibody Hz4B4-1, and the location of humanization.

The 4B4-1-1 DNA (SEQ ID NO:45 and SEQ i) NO:44, VH and VL respectively) and amino acid (SEQ ID NO:39 and SEQ ID NO:38, VH and VL respectively) sequences are shown aligned with the Hz4B4-1 DNA (SEQ ID NO:43 and SEQ ID NO:42, VH and VL respectively) and amino acid (SEQ ID) NO:2 and SEQ ID NO: 1, VH and VL respectively) sequences.

FIG. 5—Location of the primer used in PCR synthesis of the genes encoding VH and VL of humanized antibody Hz4B4-2, and the location of humanization.

The Hz4B4-1 DNA (SEQ ID NO:43 and SEQ ID NO:42, VH and VL respectively) and amino acid (SEQ ID NO:2 and SEQ ID NO:1, VH and VL respectively) sequences are shown aligned with the Hz4B4-2 DNA (SEQ ID NO:47 and SEQ ID NO:46, VH and VL respectively) and amino acid (SEQ ID NO:4 and SEQ ID NO:3, VH and VL respectively) sequences.

FIGS. 6a–6i—Change in the production level of OVA-specific IgG in baboons that have been immunized with ovalbumin and treated with humanized antibody Hz4B4-1.

Figure 7A:
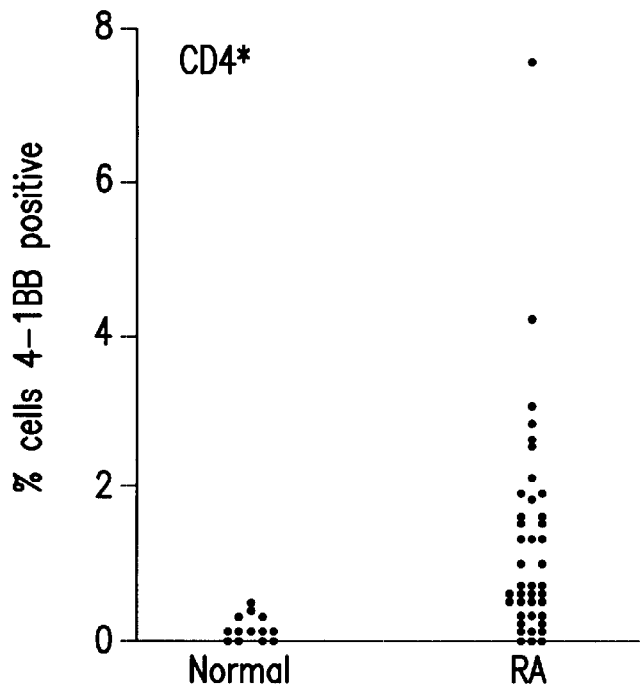
Figure 7B:
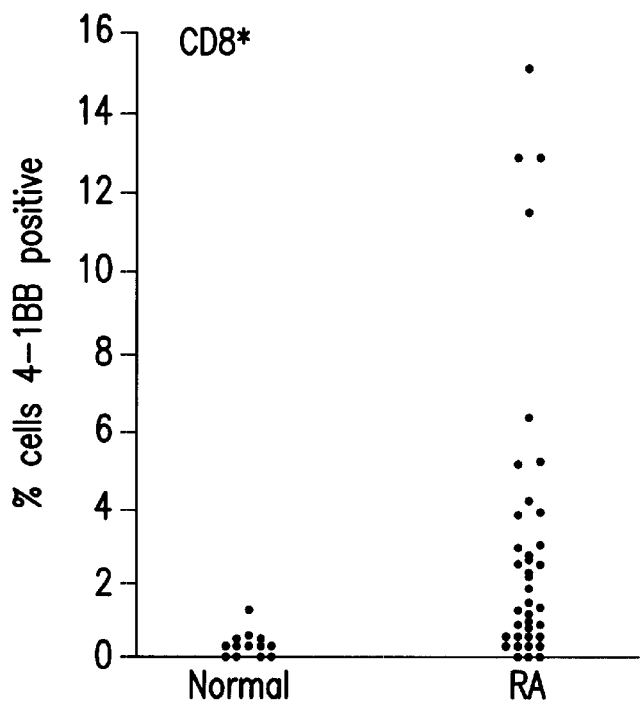
Figures 7C, 7D:
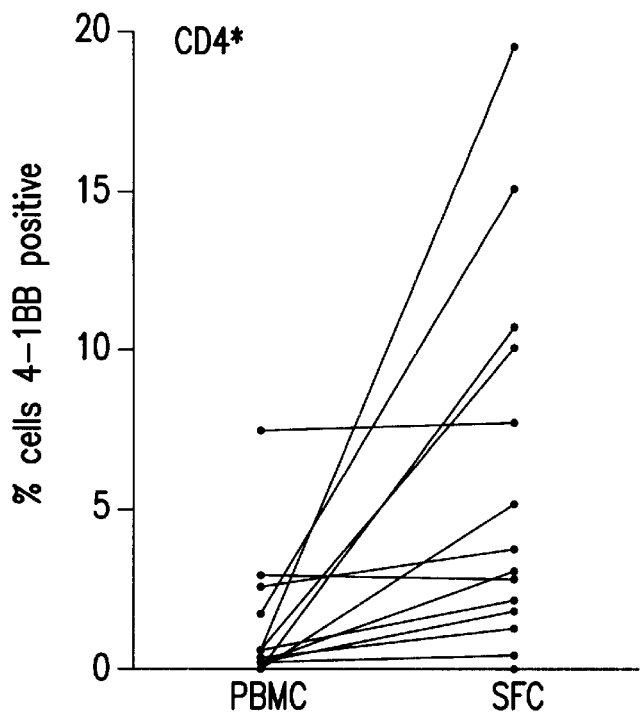

FIGS. 7a–7d—FIGS. 7a and 7b show the proportion of cells reacting with 4B4 monoclonal antibody with $CD4^+$ and $CD8^+$ T-cells from the peripheral blood of normal people and rheumatoid arthritis patients. FIGS. 7c and 7d show the proportion of cells reacting with 4B4 monoclonal antibody with $CD4^+$ and $CD8^+$ T-cells from peripheral blood and synovial fluid of normal peeople and rheumatoid arthritis patients.

DETAILED DESCRIPTION OF THE PRESENT INVENTION

The present invention is embodied in two humanized monoclonal antibodies made from mouse monoclonal antibody 4B4-1-1 (Korean patent laid open no. 96-37064) that specifically binds human 4-1BB. The humanized monoclonal antibodies were used in human tests.

The first humanized antibody Hz4B4-1 was made by grafting the antigen binding region, complementarity determining region (CDR), in the variable region of the mouse monoclonal antibody 4B4-1-1. In order to increase the antigen binding affinity of the humanized antibody, several amino acid residues were substituted in the framework region (FR) to resemble mouse antibody. The result is that the antibody has almost the same antigen binding affinity as the original mouse monoclonal antibody. The humanized antibody Hz4B4-1 is comprised of a light chain variable region having the amino acid sequence of SEQ ID NO:1 and a heavy chain variable region having the amino acid sequence of SEQ ID NO:2.

In order to make Hz4B4-1 more like a human antibody, additional amino acids in the mouse framework (FR) and complementarity determining regions (CDRs) (see, pp. 24–28 of Hood et al., "Immunology", second ed. c. 1984 by Benjamin/Cumming Publishing Co., Inc., Menlo Park, Calif., esp. FIGS. 2–6 and 2–10; and pp. 288–296 of Paul, "Fundamental Immunology", third ed. c. 1993 by Raven Press, Ltd., New York, N.Y., esp. Table 2) were substituted at several sites to resemble human antibody, and as a result the humanized antibody Hz4B4-2 was constructed. Hz4B4-2 has an antigen binding affinity that is 5 times greater than Hz4B4-1, and has 7 times higher antigen binding affinity than the original mouse monoclonal antibody. Humanized antibody Hz4B4-2 has a light chain variable region having an amino acid sequence shown in SEQ ID NO:3 and a heavy chain variable region having an amino acid sequence shown in SEQ ID NO:4.

Bacteria harboring the expression plasmid comprising the gene encoding the light chain Hz4B4-1 humanized antibody of the present invention, pRc-Hz4B4-Mok-gs, and the gene encoding the heavy chain, pCI-Hz4B4-MoH, were deposited at the Korean Institute of Science and Technology, Department of Life Sciences Institute Gene Bank, under accession numbers KCTC 0537BP and KCTC 0536BP, respectively, on October 27, 1998.

The cell line MH200-3, producing the antibody Hz4B4-1 and SB500-23, producing Hz4B4-2 were deposited at the Korean Institute of Science and Technology, Department of Life Sciences Institute Gene Bank, under the accession numbers KCTC 0540BP and KCTC 0541BP, respectively, on October 27, 1998.

The humanized antibody of the invention exhibits high affinity for human 4-1BB, as well as sequence similarity to human. antibody. The humanized antibody can be used to treat autoimmune diseases and can be used as an effective immunosuppressant without encountering adverse side-effects.

For this purpose, the humanized antibody of the invention can be used as the active ingredient in a pharmaceutical composition to treat autoimmune diseases, and can also be used as an immunosuppressant. The pharmaceutical composition can be formulated as an oral or non-oral dosage form, for immediate or extended release. The composition can comprise inactive ingredients ordinarily used in pharmaceutical preparation such as diluents, fillers, disintegrants, sweeteners, lubricants and flavors. The pharmaceutical composition is preferably formulated for intravenous administration, either by bolus injection or sustained drip, or for release from an implanted capsule. A typical formulation for intravenous administration utilizes physiological saline as a diluent.

Fab or Fab' portions of the antibodies of the invention can also be utilized as the therapeutic active ingredient. Preparation of these antibody fragments is considered known in the art.

Formulation of antibodies for therapeutic administration is considered known in the art.

The dose for a patient population depends upon the specific antibody used, body weight, age, gender, state of health, diet, administration time and formulation of the composition, route of administration, and the disease to be treated. A typical dose is from 0.1 mg/kg/day to 100 mg/kg/day. More typically the dose is from 1 mg/kg/day to 50 mg/kg/day.

The composition of the present invention can also include printed matter that describes clinical indications for which the antibodies can be administered as a therapeutic agent, dosage amounts and schedules, and/or contraindications for administration of the antibodies of the invention to a patient.

The antibodies of the invention can also be used in a diagnostic assay. One preferred format for a diagnostic assay of the invention is quantitation of cells in a sample that express h4-1BB on their surface. Methods for counting cells bearing particular surface markers are well-known in the art. For example, fluorescence activated cell sorting can be used. Another format for a diagnostic assay of the invention is to quantitate the amount of h4-1BB protein in a sample. There are many formats for performing such an assay known in the art, for example antigen-immobilized or sandwich format enzyme-linked immunosorbent assays.

The invention is illustrated by the following Examples. The Examples are offered by way of illustration of the present invention, and not by way of limitation.

EXAMPLE 1

Design of the Humanized Antibody Hz4B4-1

In order to construct a humanized antibody, the amino acid sequences of the light chain and heavy chain variable regions of the mouse monoclonal antibody 4B4-1-1 (Korean laid-open application no. 96-37064) were compared with human sequences in the GenBank database. The human heavy chain variable region sequence M17750 (Dersimonian, H. et al., *J. Immunol.*, 139, 2496 (1987)) having the greatest sequence similarity to the mouse 4B4-1-1 antibody heavy chain, and human light chain variable region sequence X82934 (Esposito, G. et al., *Arch. Virol.*, 142, 601 (1997)) that has the most similarity to the mouse 4B4-1-1 antibody light chain were selected. In order to humanize the mouse monoclonal antibody 4B4-1-1, the CDR from the mouse antibody was grafted on to a human antibody. Also, 10 critical residues in the FR region of humanized light chain and 11 critical residues in the FR region of the humanized heavy chain were substituted with corresponding amino acids from the mouse 4B4-1-1 antibody.

The humanized antibody Hz4B4k-1 light chain variable region designed as above and humanized heavy chain variable region Hz4B4h-1 have the sequences designated SEQ ID NO:1 and SEQ ID NO:2, respectively. These sequences are compared with a light chain variable region sequence (SEQ ID NO:38) and a heavy chain variable region sequence (SEQ ID NO:39) of the mouse monoclonal antibody 4B4-1-1. These sequences are further compared to a light chain variable region sequence X82934 (SEQ ID NO:40) and a heavy chain variable region sequence M17750 (SEQ ID NO:41) of a human antibody. The alignment is shown in FIG. 1.

EXAMPLE 2

Construction of the Gene Encoding Humanized Antibody Hz4B4-1 and the Expression Plasmid Primers were made that encompassed the base sequences in the regions in which the replacements were desired. These primers were KXA (SEQ ID NO:5), KXB (SEQ ID NO:6), KXC (SEQ ID NO:7), KXD (SEQ ID NO:8), KXE (SEQ ID NO:9), KXF (SEQ ID NO:10), KXG (SEQ ID NO:11), KXH (SEQ ID NO:12), AMH (SEQ ID NO:13), BMH (SEQ ID NO:14), CMH (SEQ ID NO:15), DMH (SEQ ID NO:16), EMH (SEQ ID NO:17), FMH (SEQ ID NO:18), GMH (SEQ: ID NO:19), HMH (SEQ ID NO:20).

Figure 2:
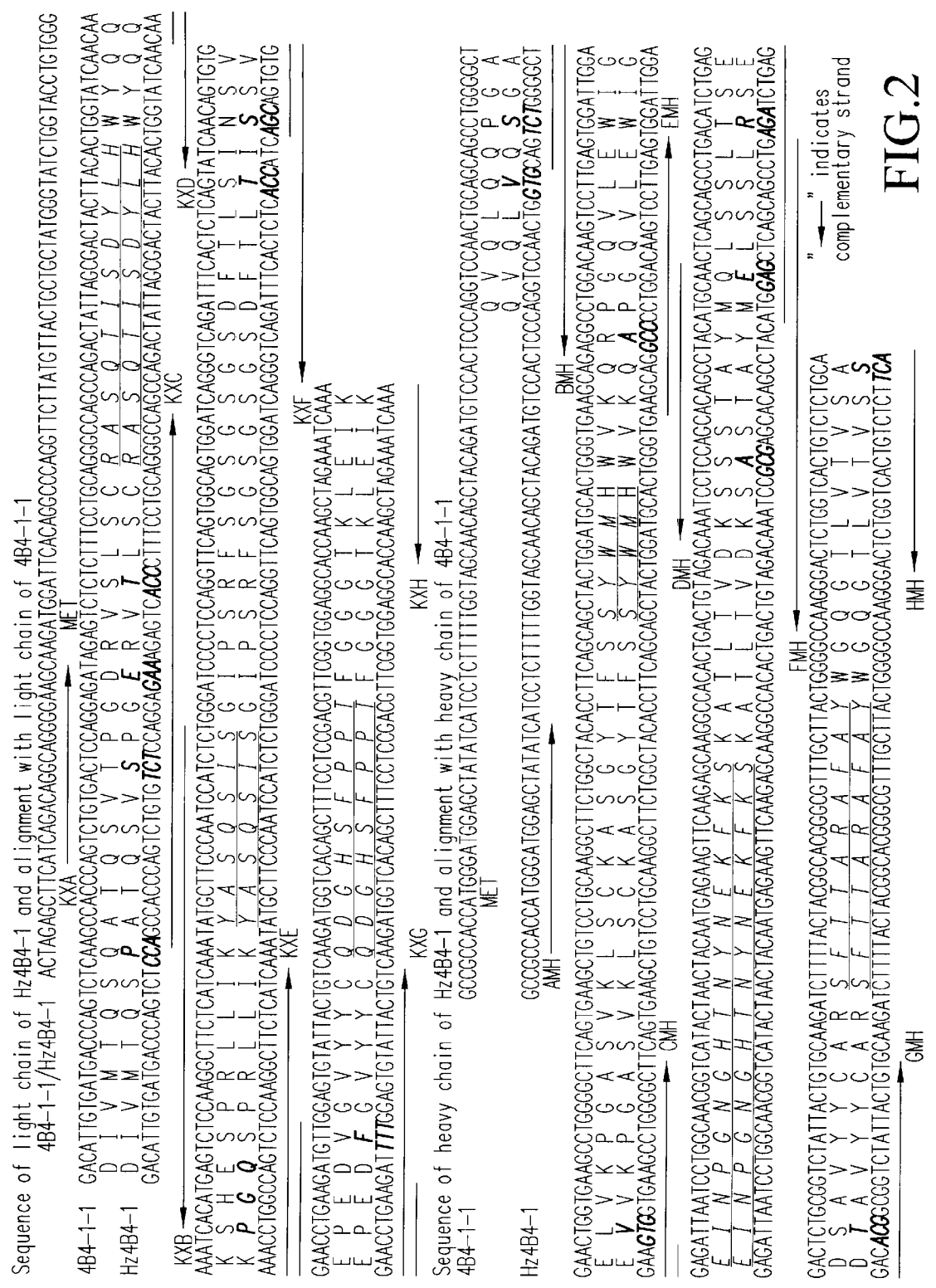

Among the above-described primers, the primers KXA (SEQ ID NO:5) to KXH (SEQ ID NO:12) were used to construct the gene encoding a humanized kappa light chain variable region. Primers AMH (SEQ ID NO:13) to HMH (SEQ ID NO:20) were used to construct the gene encoding a humanized heavy chain variable region. FIG. 2 shows by the location of the primers the regions of humanization in the humanized antibody Hz4B4-1, including the genes encoding the VL (SEQ ID NO:42), and the VH (SEQ ID NO:43). For comparison, FIG. 2 also shows the gene sequences of the light chain variable region (SEQ ID NO:44) and heavy chain variable region (SEQ ID NO:45) of the mouse monoclonal antibody 4B4-1-1.

The above primers were used to perform a polymerase chain reaction (PCR) using DNA encoding the light and heavy chain variable regions of the mouse monoclonal antibody to 4-1BB (Korean laid open patent no. 96-37064). The products were joined by an ordinary recombinant PCR method to form complete VL and VH cDNAs.

The PCR products of the humanized VL was cut with Hind III, then blunt ended with Klenow enzyme, and then cut again with Bgl II. The PCR product encoding VL that was made from primer HKD (SEQ ID NO:22) and primer Ryu-93 (SEQ ID NO:48), using the human VL (HCk) containing plasmid pAcS2-CK (Jin et al., *Virus Research*, 38:269–277 (1995)) as a template was inserted into a pBluescript™ plasmid. The so-constructed pBS-Ck plasmid was cut with SpeI, and blunt ended with Klenow enzyme, and then cut with BglII. Thus, the plasmid pBS-Vk-Ck that contains the humanized VL was constructed.

Figure 3:
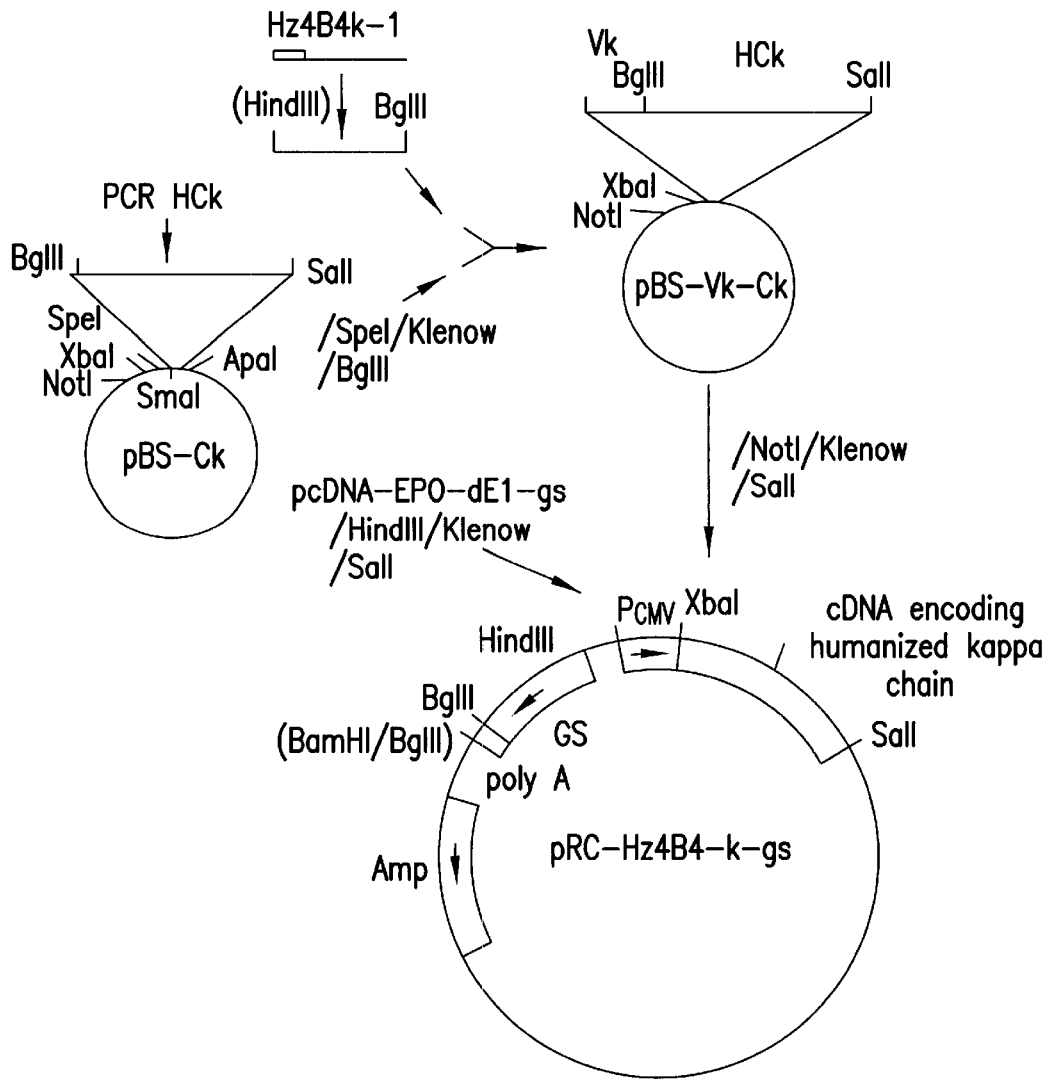
FIG. 3—Construction of the expression plasmid pRc-Hz4B4-k-gs and its restriction enzyme map.

To insert the humanized VL into an expression vector, the EPO gene-containing HindIII-SalI fragment was removed from plasmid pcDNA-EPO-dE1-gs (Korean patent application no. 97-76923), and replaced with the humanized VL cDNA containing the NotI-SalI fragment from the plasmid pBS-Vk-Ck. The resultant plasmid is called pRc-Hz4B4-k-gs. Details of the construction of the expression plasmid pRc-Hz4B4-k-gs, and its restriction enzyme map are shown in FIG. 3.

Figure 4:
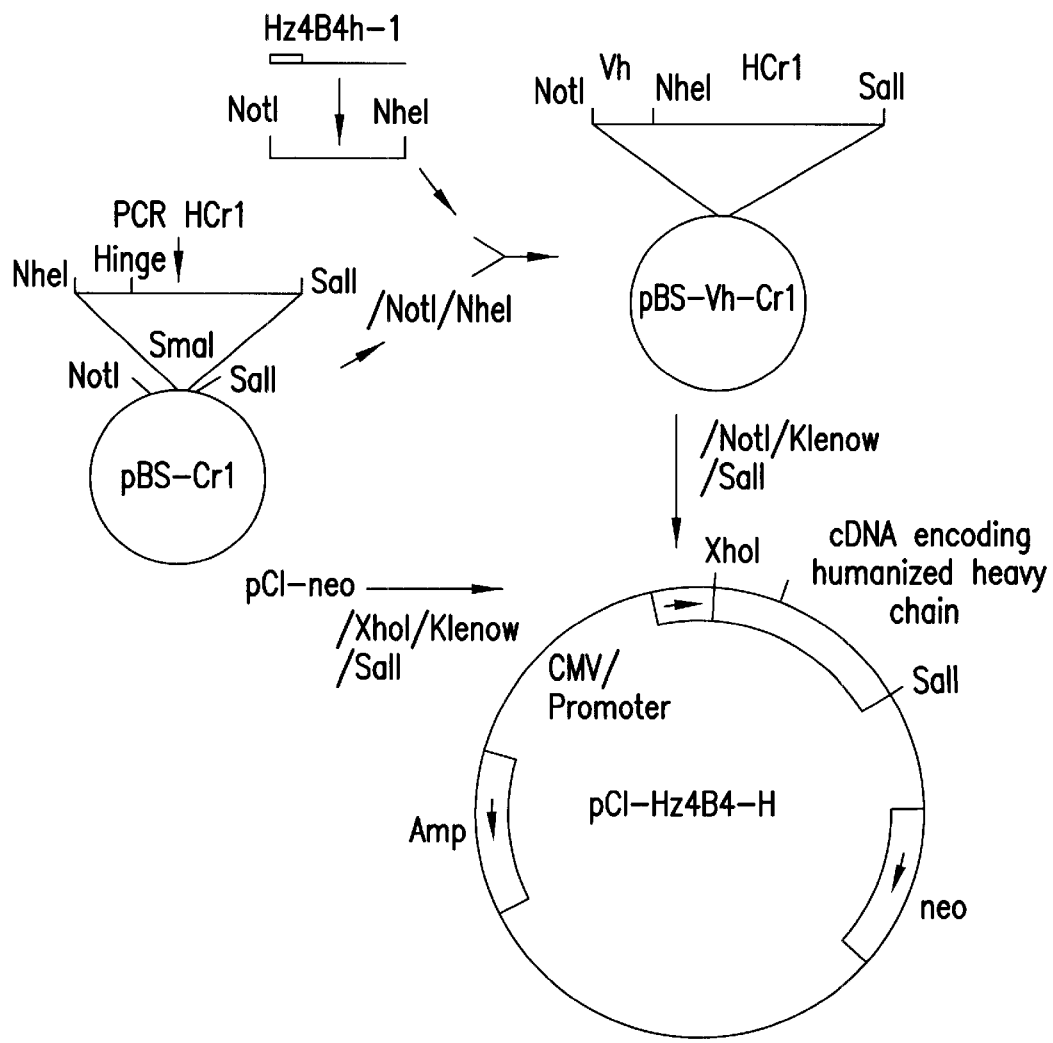
FIG. 4—Construction of the expression plasmid pCI-Hz4B4-H and its restriction enzyme map.
Figure 6A:
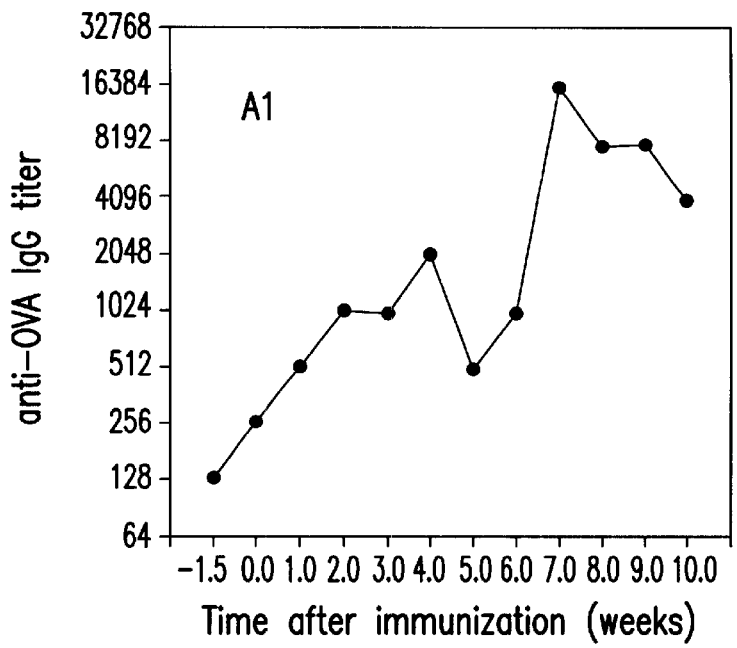
Figure 6B:
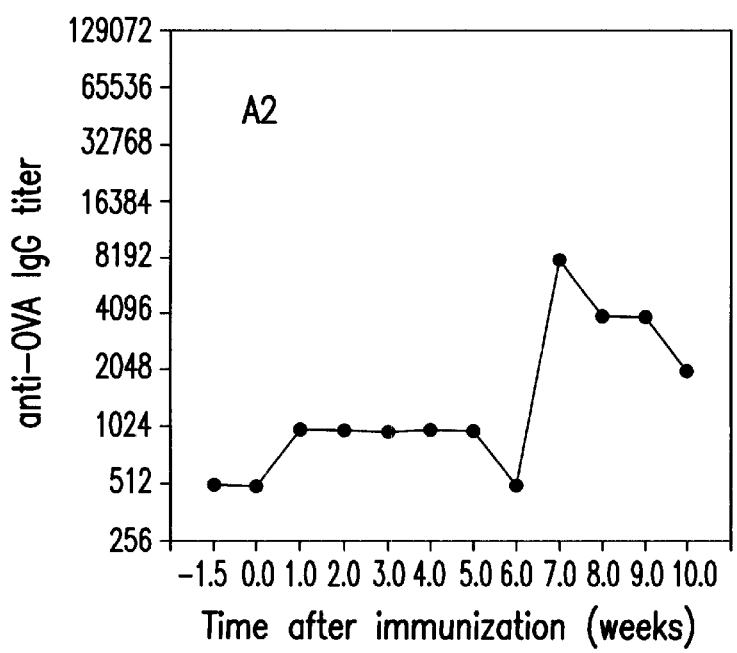
Figure 6C:
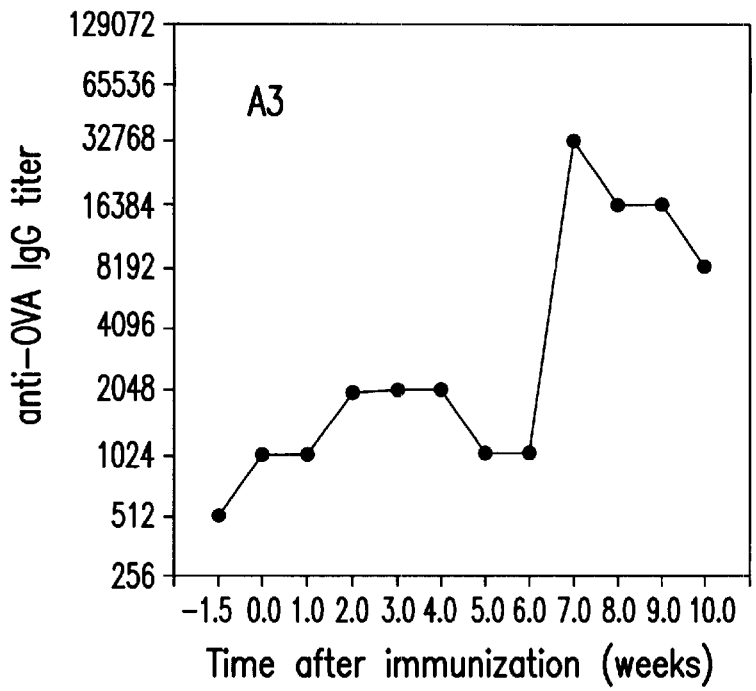
Figure 6D:
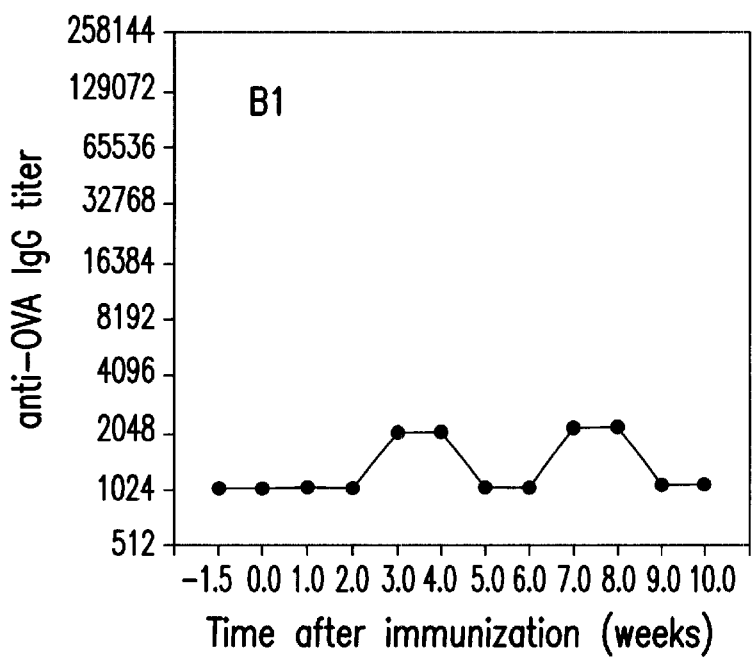
Figure 6E:
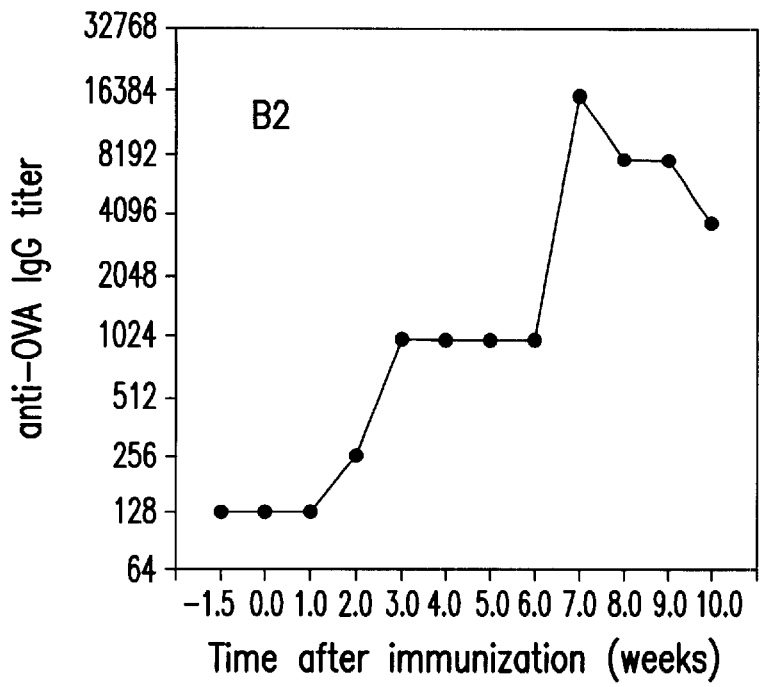
Figure 6F:
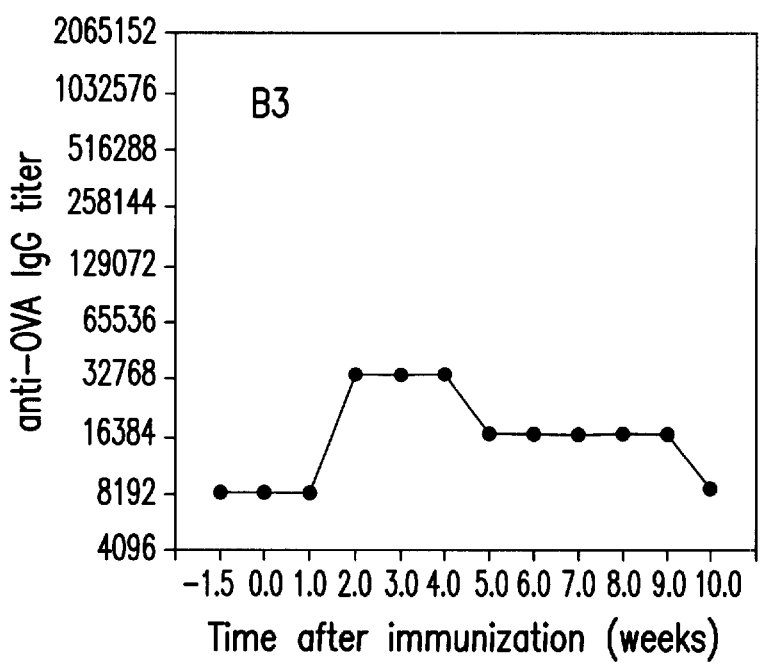
Figure 6G:
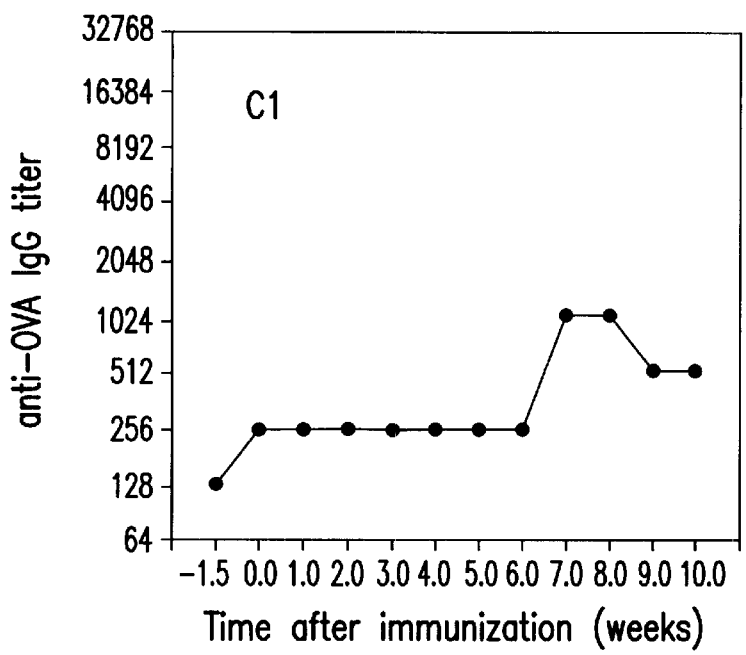
Figure 6H:
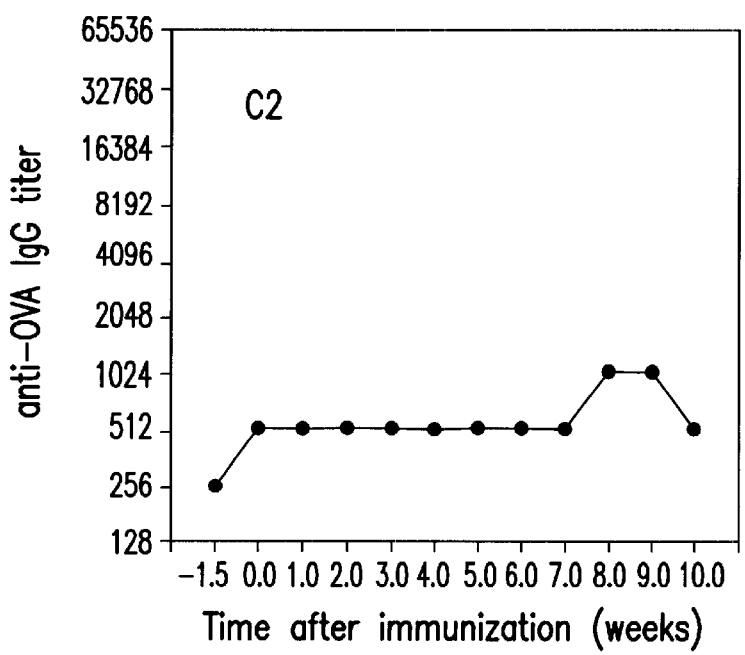
Figure 6I:
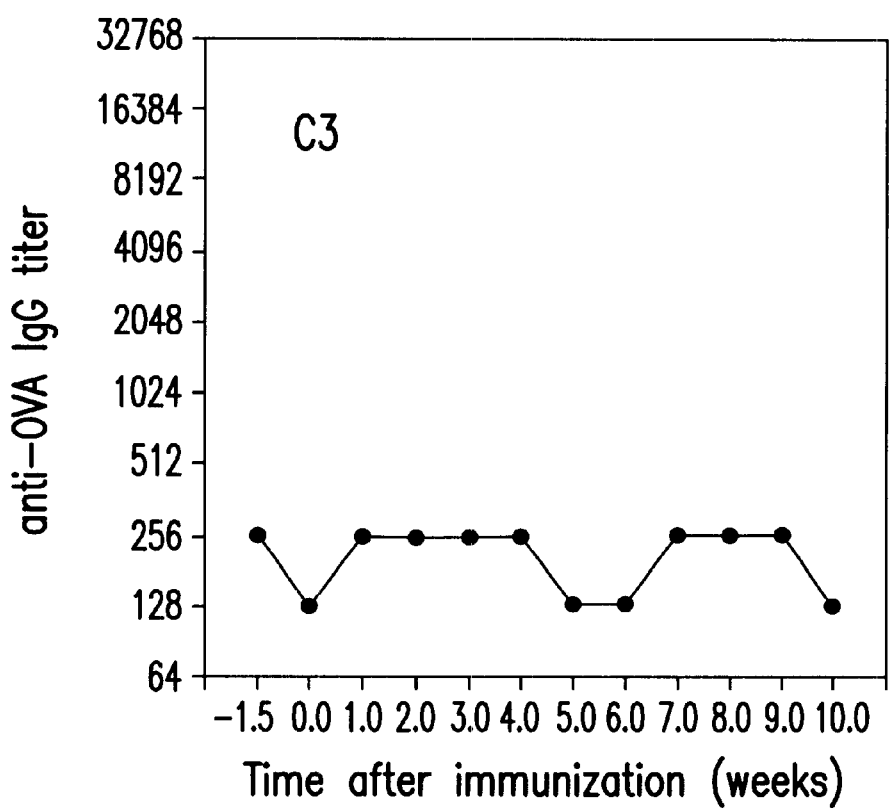

To construct the heavy chain, similarly made PCR products of VH were cut with NotI and NheI. Then, the PCR product cDNA encoding the VH made from the plasmid pAcS2-CH (Jin et al., *Virus Research*, 38:269–277 (1995)), containing a human antibody VH gene, using primer HHCD (SEQ ID NO:21) and primer Ryu-101 (SEQ ID NO:49), was inserted into a pBluescript™ plasmid. The plasmid pBS-Cr1 resulted. PBS-Cr1 was digested with NotI and NheI, and the plasmid pBS-Vh-Cr1 was constructed. In order to insert the gene encoding the humanized. heavy chain into an expression vector, pBS-Vh-Cr1 as digested with NotI, and blunt ended with Klenow, and then digested again with SalI, and then inserted into the XhoI-SalI site of the plasmid pCI-neo, which resulted in the plasmid pCI-Hz4B4-H. The details of the construction of the plasmid pCI-Hz4B4-H and its restriction enzyme map are shown in FIG. 4.

The base sequence of the gene encoding the humanized light and heavy chains from each plasmid was confirmed by DNA sequence analysis. The humanized light and heavy chain genes in the expression plasmids were linked to a human cytomegalovirus (HCMV) promoter.

EXAMPLE 3

Expression of Humanized Antibody Hz4B4-1 and Selection of Cells

CHO-K1 cells (ATCC CCL61) cultured in GDMEM containing 10% dialyzed calf serum (FBS) in 5% $CO_2$ at 37°C., were inoculated into a 6 cm diameter dish so that $5 \times 10^5$ cells were obtained. GDMEM contains DMEM (Gibco) and 4.5 g/l glucose,15 mg/l phenol red, 1 mM sodium pyruvate, 1.75 g/l sodium bicarbonate, 500 μM asparagine, 30 μM adenosine, 30 μM guanosine, 30 μM cytidine, 30 μM uridine, 10 μM thymidine, and non-essential amino acids (GIBCO). 2.5 μg of plasmid pRc-Hz4B4-k-gs and 2.5 μg of pCI-Hz4B4-H made in Example 2 were combined and diluted in 0.3 ml OPTI-MEM I™ (GIBCO). Also, in 0.3 ml of OPTI-MEM I™, 15 μl of lipofectamine™ (GIBCO) was diluted, mixed, and allowed to stand for 15 min.

The prepared CHO-K1 cells were washed 3 times in OPTI-MEM I™. Next, the plasmid-lipofectamine™ mixture prepared as above was spread evenly over the cells. The cells were cultured in 5% $CO_2$ at 37°C. for 6 hr. Then, the culture medium was changed to 3 ml of GDMEM containing 10% dialyzed calf serum, and the cells were cultured for an additional 48 hrs. In the culture medium, 3 ml of 0.25% trypsin (GIBCO) was added at 37° C. and allowed to react for 3 minutes, and centrifuged (1,000×g, 5 min.). The cells thus obtained were placed into 96-well plates at $2 \times 10^3$ cells per well. After 48 hr, 5 μM methionine sulfoxamine (MSX) was added to the GDMEM containing 10% dialyzed calf serum and the cells were cultured in 5% $CO_2$ at 37°C. The culture medium was changed every 4 days; the culture was continued for 2 weeks.

The ability of each surviving cell clone to produce antibodies was assayed. An ELISA sandwich assay using goat anti-human IgG (Sigma) conjugated to horseradish peroxidase (HRP) (Park et al., *Hybridoma*, 15, 435–441 (1996)) was carried out to obtain clones producing antibodies. Among these, 5 clones (A6B, A9A, B1F, 212A, A7B) exhibited high production of antibodies. These 5 clones were placed in GDMEM containing 10% dialyzed calf serum. 100, 200, 350, 500 and 1000 μM MSX was added to each culture, and the cell clones that were most viable and that produced the most highest amount of antibodies were determined and separated out. The 3 clones that produced the largest amount of the product are shown in Table 1.

TABLE 1

| Clone | Conc. of MSX (μM) | Production of Ab (μg/$10^6$ cells/day) |
|---|---|---|
| A6B-200-2 | 200 | 11.3 |
| MH200-2 | 200 | 12.2 |
| MH200-3 | 200 | 16.2 |

EXAMPLE 4

Isolation and Purification of Humanized Antibody Hz4B4-1

The cells of the clone MH200-3 obtained in Example 3 were cultured in T175 flasks containing serum-free media (CHO-S-SFMII, GIBCO) in 5% $CO_2$ at 37° C. The culture conditioned medium was applied to a Protein G-Sepharose column (Pharmacia). The antibodies that bound to the column were eluted with 0.1 M glycine (pH 2.7), neutralized with 1M Tris (pH 9.0), and dialyzed with PBS buffer (pH 7.0). The purified antibodies were electrophoresed on 10% SDS-PAGE. Bands of about 55 kDa (heavy chain) and about 25 kDa (light chain) were observed indicating that the humanized antibodies were purified.

EXAMPLE 5

Antigen-binding Affinity of Humanized Antibody Hz4B4-1

The binding affinity of the mouse monoclonal antibody 4B4-1-1 and humanized antibody were determined and compared using the BIAcore™ assay (Pharmacia). Rabbit anti-mouse IgG (Sigma) and goat anti-human IgG (Fc-specific) were each diluted in 10 mM acetic acid buffer, and coupled to a Dextran CM-5 sensor chip (Pharmacia). 1 M ethanolamine was added to stop the reaction. Mouse monoclonal antibody 4B4-1-1 and humanized antibody Hz4B4-1 were each diluted to a concentration of 50 μg/ml in HEPES buffer (HBS). The coupled antibodies were bound at 100 resonance units (R.U.), and 25 μg/ml of 4-1BB antigen was applied at a flow rate of 10 μl/min. and bound for 5 minutes. HBS buffer (Pharmacia) was applied for 5 minutes at the same flow rate so that dissociation would occur. The association rate and dissociation rates and corresponding rate constants were determined by using BIA evaluation software. The results are shown in Table 2 as $k_{on}$ and $k_{off}$ values; $K_d$ is also shown.

TABLE 2

Antigen binding affinity of humanized antibody Hz4B4-1

| Antibody | $k_{on}$ (M$^{-1}$s$^{-1}$) | $k_{off}$ (s$^{-1}$) | $K_d$ (M) |
|---|---|---|---|
| Mouse monoclonal antibody 4B4-1-1 | $1.16 \times 10^4$ | $1.54 \times 10^{-6}$ | $1.33 \times 10^{-10}$ |
| humanized antibody Hz4B4-1 | $5.00 \times 10^4$ | $4.36 \times 10^{-6}$ | $8.72 \times 10^{-11}$ |

The results above show that the humanized antibody Hz4B4-1 has greater association and dissociation rate with the antigen compared with the mouse antibody. The antigen binding affinity ($K_d$) was about 1.5 times greater than the mouse antibody.

EXAMPLE 6

Design of the Humanized Antibody Hz4B4-2

In order to humanize HzHB4-1 even more, one amino acid residue in CDR1 of the light chain, and 8 amino acid residues in the mouse FR were replaced with corresponding human amino acid residues. Also, 4 amino acid residues were replaced in CDR2 of the humanized heavy chain, and 8 amino acid residues were replaced in the mouse FR with 15 corresponding residues from a human antibody. As indicated above, the novel humanized light chain Hz4B4k-2 and humanized heavy chain Hz4B4h-2 have the amino acid sequence of SEQ ID NOS:3 and 4, respectively. These sequences were aligned with mouse monoclonal antibody 4B4-1-1 VL (SEQ ID NO:38) and VH (SEQ ID NO:39), human antibody VL X82934 (SEQ ID NO:40) and VH M17750 (SEQ ID NO:41), and Hz4B4-1 humanized antibody sequences (SEQ ID NOS:1 and 2), The alignment is shown in FIG. 1.

EXAMPLE 7

Construction of the Gene Encoding Humanized Antibody Hz4B4-2 and the Expression Plasmid Primers were synthesized that encompassed the base sequences in the regions in which the substitutions were desired. These primers were MOKA (SEQ ID NO:23), MOKB (SEQ ID NO:24), MOKC (SEQ ID NO:25), MOKD (SEQ ID NO:26), MOKE (SEQ ID NO:27), MOKF (SEQ ID NO:28), MOKG (SEQ ID NO:29), MOKH (SEQ ID NO:30), MOHA (SEQ ID NO:31), MOHB (SEQ ID NO:32), MOHC (SEQ ID NO:33), MOHD (SEQ ID NO:34), MOHE (SEQ ID NO:35), MOHF (SEQ ID NO:36), MOHG (SEQ ID NO:37).

Figure 5:
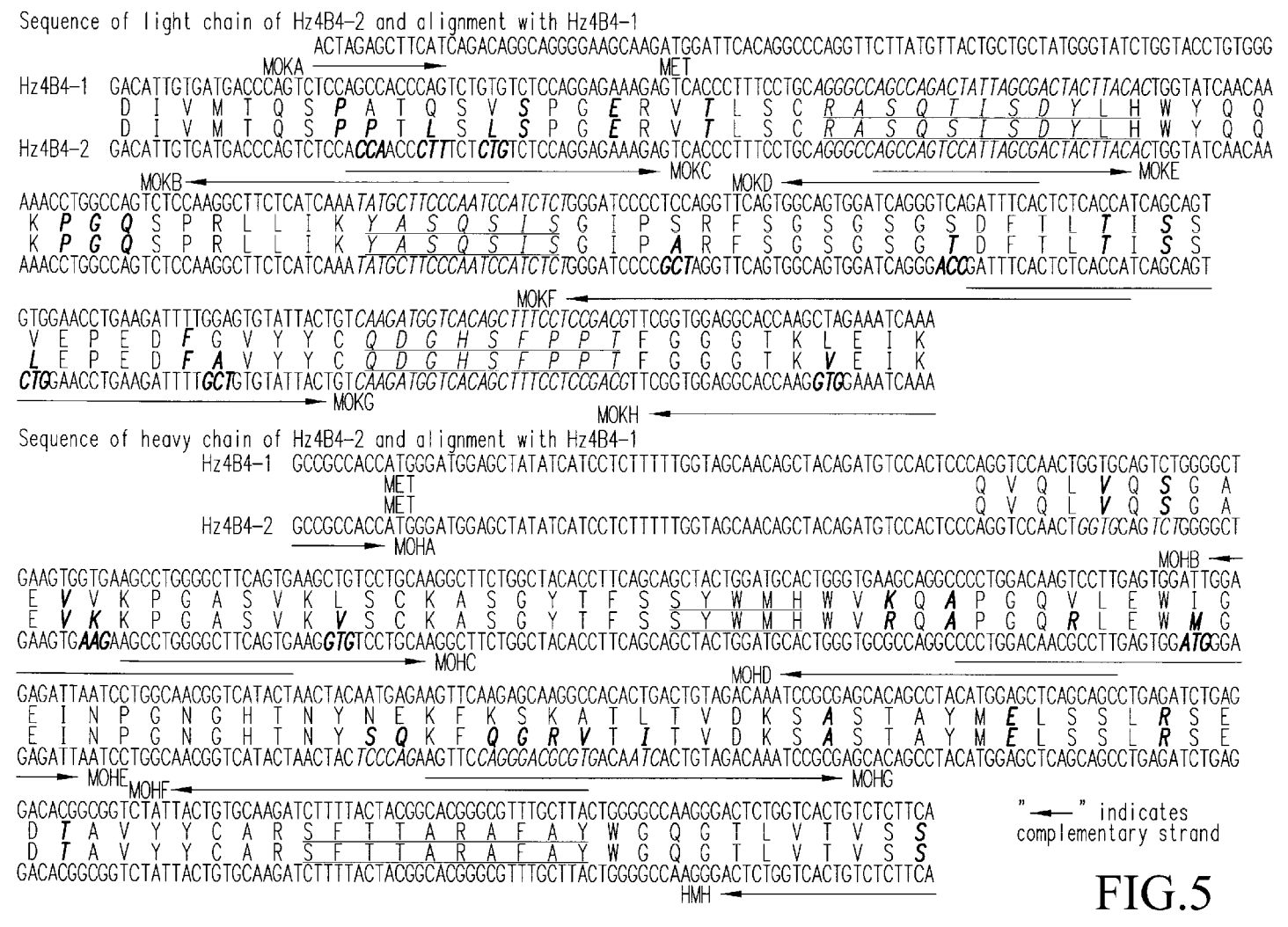

Among the above primers, MOKA (SEQ ID NO:23) to MOKH (SEQ ID NO:30) were used to construct the gene encoding humanized kappa light chain variable region. Primers MOHA (SEQ ID NO:31) to MOHG (SEQ ID NO:37) were used to construct the gene encoding the humanized heavy chain variable region. In addition, primer HMH (SEQ ID NO:20) was also used in the construction of the gene encoding humanized heavy chain variable region. FIG. 5 shows the humanized region of Hz4B4-1, and the VL gene (SEQ ID NO:42) and VH gene (SEQ ID NO:43) of Hz4B4-1.

The above MOK* series of primers were used with the light chain gene of the Hz4B4-1 antibody as a template to produce a gene encoding the light chain of the humanized antibody for Hz4B4k-2. The above MOH* series of primers was used with the heavy chain gene of Hz4B4-1 as a template to produce a VH gene and an ordinary recombinant PCR method was carried out to further humanize the antibody. The genes encoding VL (Hz4B4k-2, SEQ ID NO:46) and VH (Hz4B4h-2, SEQ ID NO:47) were synthesized. The Hz4B4k-2 DNA obtained above was cut with XbaI and BglII and inserted into the XbaI/BglII site of the Hz4B4-1 light chain expression vector, pRC-Hz4B4-k-gs. Thus, the Hz4B4-2 light chain expression plasmid pRc-Hz4B4MoK-gs was constructed.

In the case of the heavy chain, the Hz4B4h-2 DNA was cut with XhoI and NheI, and inserted into the XhoI/NheI site of the heavy chain expression vector pCI-Hz4B4-H. Thus, the humanized antibody Hz4B4-2 heavy chain expression plasmid pCI-Hz4B4-MoH was constructed.

The base sequence of the gene encoding the humanized light and heavy chains from each plasmid was confirmed by DNA sequence analysis.

EXAMPLE 8

Expression of Humanized Antibody Hz4B4-2 and Selection of Cells

As in Example 3 above, CHO-K1 cells were transfected with pRc-Hz4B4-Mok-gs and pCI-Hz4B4-MoH, and the transformed cells were incubated for 2 weeks in GDMEM culture medium that contains 25 μM methionine sulphoximine (MSX), at 37° C., in 5% $CO_2$. Resistant clones were isolated, and antibody production was determined by sandwich ELISA. Among these clones, the high producing SB clones were cultured in GDMEM medium that contains 10% dialyzed calf serum, to which 100, 200, 350, 500 or 1000 μM MSX was added. The clones that were most viable and high antibody producers at 500 μM MSX were separated out. These clones produced about 3 μg/$10^6$ cells/day of antibody.

EXAMPLE 9

Isolation and Purification of Humanized Antibody Hz4B4-2

As in Example 4, the above SB500 cells were cultured in serum-free medium. The conditioned culture medium was applied to a protein G-Sepharose (Pharmacia) affinity column. The purified antibodies were electrophoresed on 10% SDS-PAGE. Bands of about 55 kDa (heavy chain) and about 25 kDa (light chain) were observed, indicating that the humanized antibodies had been purified.

EXAMPLE 10

Antigen-binding Affinity of Humanized Antibody Hz4B4-2

The antigen binding affinity of the purified Hz4B4-2 humanized antibody was measured as in Example 5 using the BIAcore™ assay (Pharmacia). The results are shown in Table 3.

TABLE 3

Antigen binding affinity of humanized antibody Hz4B4-2

| Antibody | $k_{on}$ (M$^{-1}$s$^{-1}$) | $k_{off}$ (s$^{-1}$) | $K_d$ (M) |
|---|---|---|---|
| Mouse monoclonal antibody 4B4-1-1 | $1.16 \times 10^4$ | $1.54 \times 10^{16}$ | $1.33 \times 10^{-10}$ |
| humanized antibody Hz4B4-1 | $5.00 \times 10^4$ | $4.36 \times 10^{-6}$ | $8.72 \times 10^{-11}$ |
| humanized antibody Hz4B4-2 | $1.17 \times 10^4$ | $2.14 \times 10^{-6}$ | $1.83 \times 10^{-11}$ |

As shown in Table 3, Hz4B4-1 has 1.5 times greater antigen binding affinity ($K_d$) compared to mouse monoclonal antibody 4B4-1-1. Humanized antibody Hz4B4-2 has 7.3 times greater antigen binding affinity compared the mouse monoclonal antibody. It is expected that the humanized antibodies Hz4B4-1 and Hz4B4-2 of the invention will have the same affinity in human beings.

EXAMPLE 11

Experimental Results—Immune Response to and Immunosuppressive Effect of the Humanized Antibody A. Immune Response in Baboon and Administration of the Humanized Antibody Hz4B4-1

Seven- to eight-year-old male and female baboons (*P. anubis*), weighing 12 to 15 kg, at the Southwest Foundation for Biomedical Research (San Antonio, Tex.), were used. The baboons were divided into three groups of two males and one female per group, and maintained under standard animal housing conditions. Each animal was immunized intramuscularly with 1 mg of OVA (Sigma) emulsified in aluminum hydroxide (Sigma) The time of OVA-immunization was designated as week: 0, and OVA (1 mg in PBS) was given again at week 6. The first injection of humanized antibody (or PBS, control group) was given at the time of the first OVA-immunization (week 0), and subsequent injections of humanized antibody or PBS were given at weeks 1, 2, 3, 6, 7, 8, and 9. The first group of three baboons (control group) was injected intravenously with 10 ml PBS. The second and third groups were treated with the humanized antibody Hz4B4-1 obtained in Example 4, at 1 or 4 mg/kg of body weight, respectively. Blood samples were collected at week −1.5, week 0, and at weekly intervals until week 10.

B. Evaluation of Host Humoral Immune Response

Anti-OVA and IgM levels were determined by ELISA. Immunomaxisorp™ plates (Nunc InterMed, Rockilde, Denmark) were coated with OVA at a concentration of 500 ng/well. After blocking with 1% bovine serum albumin, serial twofold dilutions of serum samples obtained in step 1 above, starting at 1/32 dilution, were added to the wells at 0.1 ml per well. The plates were incubated for 4 hours at room temperature. Bound IgG and IgM were detected with alkaline phosphatase (AP)-conjugated rabbit anti-monkey IgG (Sigma) or AP-conjugated goat anti-human IgM (Sigma), respectively by adding 0.1 ml of the conjugates to each well and incubating at the above temperature. $A_{405}$ was read by an automatic microplate reader (Molecular Devices Corp., Menlo Park, Calif.). IgG or IgM titer was determined at the highest dilution, which gave the absorbance three or five times the background reading at $A_{405}$, respectively.

Total IgG or Hz4B4-1 in the sera was quantified by ELISA. Diluted serum samples were added as above to the plates coated with goat anti-human IgG (150 ng/well) or GST-4-1BB (100 ng/well) and incubated for 4 hours at the above indicated temperature. After incubation, AP-conjugated goat anti-human IgG (Sigma) was added to each well of the plates and development of the reaction was performed using p-nitrophenyl phosphate, using an automatic microplate reader at $A_{405}$. The results are shown in Table 4 and FIGS. 6*a* to 6*i*. The concentrations of total IgG or Hz4B4-1 in each sample was calculated with reference to standard curves generated by using human IgG or purified Hz4B4-1, respectively.

TABLE 4

| Exp. Animal No. | Dose of Hz4B4-1 (mg/kg) | Ratio of OVA-specific IgG titer at wk 7 to OVA-specific IgG titer at wk 0 | Ratio of OVA-specific IgM titer at wk 7 to OVA-specific IgM titer at wk 0 | Ratio of serum conc. of total IgG at wk 7 to serum conc. of total IgG at wk 1 | Serum conc. of Hz4B4-1 at wk 1 (µg/ml) |
|---|---|---|---|---|---|
| A1 | 0 | 64 | 2 | 1.13 | — |
| A2 | 0 | 16 | 1 | 1.02 | — |
| A3 | 0 | 32 | 1 | 1.05 | — |
| B1 | 1 | 2 | 1 | 0.96 | 6.66 |
| B2 | 1 | 128 | 1 | 1.06 | 0.42 |
| B3 | 1 | 2 | 1 | 1.01 | 3.85 |
| C1 | 4 | 4 | 2 | 1.09 | 25.74 |
| C2 | 4 | 1 | 0.5 | 1.16 | 10.14 |
| C3 | 4 | 2 | 1 | 1.09 | 14.49 |

A distinguishable increase of the anti-OVA IgG level in the serum was found in the control group. The highest titers were observed at week 7, a week after the second immunization with OVA, and were 64-, 16-, and 32-fold greater than the titer at week 0 in baboons A1, A2, and A3, respectively (Table 4 and FIGS. 6*a*, 6*b*, and 6*c*). In contrast, significant suppression of the OVA-spedific Ab response was found in Hz4B4-1-treated baboons. In the second group, which was treated with a dose of 1 mg/kg of Hz4B4-1, two of three baboons (B1 and B3) showed the suppression. The titers at week 7 were twofold higher than those at week 0 (Table 1, and FIGS. 6*d*, 6*e*, and 6*f*). However, the suppression was not detected in baboon B2, which showed a 128-fold increase in titer between week 7 and week 0. In the case of the third group, which was treated with 4 mg/kg of Hz4B4-1, the suppression was shown in all three baboons. The titer increase was four-, one-, and two-fold for baboons C1, C2, and C3, respectively (Table 1, and FIGS. 6g, 6h, and 6i).

No distinguishable increase in anti-OVA IgM titer was observed in any of the animals, irrespective of whether they were treated with Hz4B4-1, indicating that Hz4B4-1 treatment did not affect the IgM production at a detectable level. Taken together, the data suggest that a state of humoral unresponsiveness to OVA, a T cell-dependent antigen, was induced by Hz4B4-1 treatment. This was further indicated by measuring the serum concentration of Hz4B4-1. The serum concentration of Hz4B4-1 was highest at week 1 in all baboons. The concentration of Hz4B4-1 in the serum of baboon B2, which did not show OVA-specific IgG suppression, was significantly lower compared with those of baboons B1 and B3 treated with the same dose of Hz4B4-1 (Table 1).

The amount of total IgG at week 0 was compared with that of week 7 in each baboon. As shown in Table 1, the total IgG amount was little altered, regardless of the treatment with Hz4B4-1. In addition, during the treatment with Hz4B4-1, no significant variations were observed in total numbers and proportions of B and T cells in each blood sample analyzed by flow cytometry. Collectively, the data indicated that the immune unresponsiveness by treatment with Hz4B4-1 was Ag-specific, and not due to overall immune suppression.

C. Analysis of 4-1BB-positive T-cells

To evaluate the clinical significance of 4-1BB molecules, the expression of these molecules on T lymphocytes of patients with rheumatoid arthritis (RA) was analyzed by FACS analysis using 4B4 MAb. PBMC was prepared from heparinized venous blood withdrawn from normal volunteers or RA patients, and synovial cells were obtained from synovial fluid aspirated from RA patients. 5×10$^5$ PBMC or synovial cells were incubated with 5 μl of phycoerythrin (PE)-labeled anti-human CD4 or PE-labeled anti-human CD8 mouse MAb (Immune Source, Los Altos, Calif.) in a staining buffer that contains DMEM (1% BSA and 0.005% NaNH$_3$) for 30 min at 4° C. in the dark. After incubation, cells were washed with staining buffer, and then incubated with 5 μl of FITC-labeled 4B4 MAb for 30 min at 4° C. in staining buffer. The percentage of 4-1BB expressing T lymphocytes was analyzed by flow cytometry. The expression of 4-1BB molecules on T lymphocytes was analyzed on a FACStar Plus™ cytometer (Becton Dickinson & Co., Mountain View, Calif.).

The expression of these molecules on peripheral blood (PBMC) T lymphocytes of 41 RA patients was compared with those of 13 normal individuals. The results are shown in FIGS. 7a and 7b. The reactivity with 4B4 MAb of CD4 or CD8 T lymphocytes of normal individuals was very low or not observed: CD4+, <0.5%; CD8+, <1,2%. In contrast, the CD4+ or CD8+ T lymphocytes from some of the RA patients showed the increased reactivity to 4B4 MAb. In the case of CD4+ T cells, the reaction rates were above 1% in 18 of 41 patients and peaked at 7.5%. In CD8+ T cells, 17 of 38 patients showed reaction rates above 2%, with a maximum value of 15%.

RA is characterized by chronic synovitis. Affected synovial tissues are infiltrated with lymphocytes and plasma cells. This disease is initiated by activation of T lymphocytes responding to some arthritogenic agents, and T lymphocytes play a primary role in the pathogenesis of RA, indicating that T lymphocytes in synovial fluid of RA patients are in an activated state (G. S. Firestein, p. 851 in "Etiology and Pathogenesis of Rheumatoid Arthritis", 5$^{th}$ ed., W. N. Kelley et al. eds., c. 1997 by W. B. Saunders, Philadelphia, Pa.). Therefore, the expression of 4-1BB molecules in synovial fluid T lymphocytes of 13 RA patients were compared with those in the peripheral blood T lymphocytes of the same patients. The results are shown in FIGS. 7c and 7d. CD4+ and CD8+ T lymphocytes in synovial fluid showed more reactivity to 4B4 MAb than those in peripheral blood; for the CD4+ or CD8+ subset, above twofold in 8 or 9 RA patients out of 13. Each line between two circles means that the corresponding PBMC and SFC were obtained from the same patient. These findings suggest that the expression of 4-1BB may be related to the disease process of RA.

Without being bound by any theory of the invention, the inventors speculate that there are two not mutually exclusive mechanisms of the immunosuppressive effect of the Hz4B4-1. First, the antibody could interfere with 4-1BB/4-1BBL interaction that plays an important role in T cell activation. Second, the antibody could eliminate 4-1BB expressing T cells via complement-dependent cytotoxicity and antibody-dependent cellular toxicity. In many cases of T cell mediated autoimmune diseases, autoantigens are not well defined or are too diverse to manipulate the immune response against the autoantigens. In this regard, functional blocking and/or elimination of activated T cells, most of which are probably autoantigen specific in patients with autoimmune diseases, could be approaches to ameliorate the disease. The inventors have discovered that a substantial proportion of T cells in PBMC and synovial fluid from RA patients express 4-1BB, which suggests that 4-1BB could be an ideal target for antibody mediated therapy for RA since only activated T cells, possibly most pathologic T cells, express 4-1BB. In this regard, a longer expression time of 4-1BB (more than 72 hours) than those of other costimulatory molecules such as CD40L, may be another advantageous point for targeting 4-1BB with the antibody. Beyond RA, Hz4B4-1 could also be used for the treatment of other T cell mediated autoimmune diseases and graft rejections.

The present specification includes the appended Sequence Listing of 49 nucleic acid or amino acid sequences. Articles of the patent and scientific periodical literature cited herein are hereby incorporated in their entirety by such citation.

We claim:

1. A humanized antibody comprising:
   a) a light chain variable region comprising a polypeptide having the amino acid sequence of SEQ ID NO:1;
   b) a heavy chain variable region comprising a polypeptide having the amino acid sequence of SEQ ID NO:2;
   c) a light chain constant region identical to a human antibody light chain constant region; and
   d) a heavy chain constant region identical to a human antibody constant region.

2. A humanized antibody comprising:
   a) a light chain variable region comprising a polypeptide having the amino acid sequence of SEQ ID NO:3;
   b) a heavy chain variable region comprising a polypeptide having the amino acid sequence of SEQ ID NO:4;
   c) a light chain constant region identical to a human antibody light chain constant region; and
   d) a heavy chain constant region identical to a human antibody constant region.

3. The humanized antibody of claim 1 or 2 wherein the heavy chain constant region is a gamma 1, gamma 2, gamma 3 or gamma 4 heavy constant region.

4. The humanized antibody of claim 1 or 2, wherein the light chain constant region is a lambda or a kappa light chain constant region.

* * * * *

SEQUENCE LISTING

<160> NUMBER OF SEQ ID NOS: 49

<210> SEQ ID NO 1
<211> LENGTH: 107
<212> TYPE: PRT
<213> ORGANISM: Artificial Sequence
<220> FEATURE:

<223> OTHER INFORMATION: Description of Artificial Sequence: Variable
      region of light chain of humanized antibody
      Hz4B4-1

<400> SEQUENCE: 1

Asp Ile Val Met Thr Gln Ser Pro Ala Thr Gln Ser Val Ser Pro Gly
 1               5                  10                  15

Glu Arg Val Thr Leu Ser Cys Arg Ala Ser Gln Thr Ile Ser Asp Tyr
                20                  25                  30

Leu His Trp Tyr Gln Gln Lys Pro Gly Gln Ser Pro Arg Leu Leu Ile
            35                  40                  45

Lys Tyr Ala Ser Gln Ser Ile Ser Gly Ile Pro Ser Arg Phe Ser Gly
 50                  55                  60

Ser Gly Ser Gly Ser Asp Phe Thr Leu Thr Ile Ser Ser Val Glu Pro
 65                  70                  75                  80

Glu Asp Phe Gly Val Tyr Tyr Cys Gln Asp Gly His Ser Phe Pro Pro
                85                  90                  95

Thr Phe Gly Gly Gly Thr Lys Leu Glu Ile Lys
                100                 105

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Variable
      region of heavy chain of humanized antibody
      Hz4B4-1

<400> SEQUENCE: 2

Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Thr Phe Ser Ser Tyr
                20                  25                  30

Trp Met His Trp Val Lys Gln Ala Pro Gly Gln Val Leu Glu Trp Ile
            35                  40                  45

Gly Glu Ile Asn Pro Gly Asn Gly His Thr Asn Tyr Asn Glu Lys Phe
 50                  55                  60

Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
                100                 105                 110

Thr Leu Val Thr Val Ser Ser
            115

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Variable
      region of light chain of humanized antibody
      Hz4B4-2

<400> SEQUENCE: 3

Asp Ile Val Met Thr Gln Ser Pro Pro Thr Leu Ser Leu Ser Pro Gly
 1               5                  10                  15

Glu Arg Val Thr Leu Ser Cys Arg Ala Ser Gln Ser Ile Ser Asp Tyr

```
                  20                  25                  30
Leu His Trp Tyr Gln Gln Lys Pro Gly Gln Ser Pro Arg Leu Leu Ile
            35                  40                  45
Lys Tyr Ala Ser Gln Ser Ile Ser Gly Ile Pro Ala Arg Phe Ser Gly
        50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Asp Gly His Ser Phe Pro Pro
                85                  90                  95
Thr Phe Gly Gly Gly Thr Lys Val Glu Ile Lys
            100                 105

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Variable
      region of heavy chain of humanized antibody
      Hz4B4-2

<400> SEQUENCE: 4

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ser Ser Tyr
            20                  25                  30
Trp Met His Trp Val Arg Gln Ala Pro Gly Gln Arg Leu Glu Trp Met
        35                  40                  45
Gly Glu Ile Asn Pro Gly Asn Gly His Thr Asn Tyr Ser Gln Lys Phe
    50                  55                  60
Gln Gly Arg Val Thr Ile Thr Val Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Phe Thr Thr Ala Arg Ala Phe Ala Tyr Trp Gly Gln Gly
            100                 105                 110
Thr Leu Val Thr Val Ser Ser
        115

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primer KXA

<400> SEQUENCE: 5
actaagcttc atcagacagg cagggga                                          27

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Primer KXB

<400> SEQUENCE: 6
tggagacaca gactgggtgg ctggagactg ggtcatcaca atgtcccc                   48

<210> SEQ ID NO 7
```

```
<211> LENGTH: 48
<212> TYPE: DNA
<213> ORGANISM: Artificial Sequence
<220> FEATURE:
<223> OTHER INFORMATION: Description of Artificial Sequence: Primer KXC

<400> SEQUENCE: 7
acccagtctg tgtctccagg agaaagagtc accctttcct gcagggcc                        48

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer KXD

<400> SEQUENCE: 8
agactggcca ggttttttgtt gataccagtg                                           30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Primer KXE

<400> SEQUENCE: 9
caaaaacctg gccagtctcc aaggcttctc atc                                        33

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Primer KXF

<400> SEQUENCE: 10
ttcaggttcc acactgctga tggtgagagt gaaatctgac cc                              42

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Primer KXG

<400> SEQUENCE: 11
agcagtgtgg aacctgaaga ttttggagtg tattactgt                                  39

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer KXH

<400> SEQUENCE: 12
aggcagatct tttgatttct agcttggt                                              28

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Primer AMH

<400> SEQUENCE: 13
```

```
attagcggcc gccaccatgg gatggagcta tatc                           34

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Primer BMH

<400> SEQUENCE: 14
ttcagcccca gactgcacca gttggacctg gga                            33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Primer CMH

<400> SEQUENCE: 15
cagtctgggg ctgaagtggt gaagcctggg gct                            33

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Primer DMH

<400> SEQUENCE: 16
tccaggggcc tgcttcaccc agtgcat                                   27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Primer EMH

<400> SEQUENCE: 17
aagcaggccc ctggacaagt ccttgag                                   27

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence: Primer FMH

<400> SEQUENCE: 18
caggctgctg agctccatgt aggctgtgct cgcggatttg tctacagt            48

<210> SEQ ID NO 19
<211> LENGTH: 48
<212> TYPE: DNA
<213> ORGANISM: Artificial Sequence
<220> FEATURE:
<223> OTHER INFORMATION: Description of Artificial Sequence: Primer GMH

<400> SEQUENCE: 19
atggagctca gcagcctgag atctgaggac acggcggtct attactgt            48

<210> SEQ ID NO 20
<211> LENGTH: 31
<212> TYPE: DNA
```

<210> SEQ ID NO 20 (implied continuation)
<213> ORGANISM: Artificial Sequence
<220> FEATURE:
<223> OTHER INFORMATION: Description of Artificial Sequence: Primer HMH

<400> SEQUENCE: 20
tatagctagc tgaagagaca gtgaccagag t                               31

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Primer HHCD

<400> SEQUENCE: 21
atatgctagc accaagggcc catcggtc                                   28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Primer HKD

<400> SEQUENCE: 22
atatagatct gtggctgcac catctgtc                                   28

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Primer MOKA

<400> SEQUENCE: 23
ccgctctaga actagagctt c                                          21

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Primer MOKB

<400> SEQUENCE: 24
cagagaaagg gttggtggag actgggtcat c                               31

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Primer MOKC

<400> SEQUENCE: 25
accaaccctt tctctgtctc caggagaaag a                               31

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Primer MOKD

<400> SEQUENCE: 26
cgctaatgga ctggctggcc ctgca                                      25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Primer MOKE

<400> SEQUENCE: 27
agccagtcca ttagcgacta cttac                                           25

<210> SEQ ID NO 28
<211> LENGTH: 55
<212> TYPE: DNA
<213> ORGANISM: Artificial Sequence
<220> FEATURE:
<223> OTHER INFORMATION: Description of Artificial Sequence: Primer MOKF

<400> SEQUENCE: 28
tggtgagagt gaaatcggtc cctgatccac tgccactgaa cctagcgggg atccc          55

<210> SEQ ID NO 29
<211> LENGTH: 54
<212> TYPE: DNA
<213> ORGANISM: Artificial Sequence
<220> FEATURE:
<223> OTHER INFORMATION: Description of Artificial Sequence: Primer MOKG

<400> SEQUENCE: 29
gatttcactc tcaccatcag cagtctggaa cctgaagatt ttgctgtgta ttac           54

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Primer MOKH

<400> SEQUENCE: 30
aggcagatct tttgatttcc accttggtgc ctccaccg                             38

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Primer MOHA

<400> SEQUENCE: 31
gccgactagt ctcgaggccg ccacc                                           25

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Primer MOHB

<400> SEQUENCE: 32
actgaagccc caggcttctt cacttcagc                                       29

<210> SEQ ID NO 33
<211> LENGTH: 30
<212> TYPE: DNA
<213> ORGANISM: Artificial Sequence
<220> FEATURE:

<223> OTHER INFORMATION: Description of Artificial Sequence: Primer MOHC

<400> SEQUENCE: 33
agcctggggc ttcagtgaag gtgtcctgca                              30

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Primer MOHD

<400> SEQUENCE: 34
aaggcgttgt ccaggggcct ggcgcaccca gtg                          33

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Primer MOHE

<400> SEQUENCE: 35
ccctggacaa cgccttgagt ggatgggaga gatt                         34

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence: Primer MOHF

<400> SEQUENCE: 36
acgcgtccct ggaacttctg ggagtagtta gtatgaccgt t                 41

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Primer MOHG

<400> SEQUENCE: 37
agttccaggg acgcgtgaca atcactgtag acaaatccgc g                 41

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Variable
      region of light chain of mouse monoclonal antibody
      4B4-1-1

<400> SEQUENCE: 38

Asp Ile Val Met Thr Gln Ser Gln Ala Thr Gln Ser Val Thr Pro Gly
 1               5                  10                  15

Asp Arg Val Ser Leu Ser Cys Arg Ala Ser Gln Thr Ile Ser Asp Tyr
             20                  25                  30

Leu His Trp Tyr Gln Gln Lys Ser His Glu Ser Pro Arg Leu Leu Ile
         35                  40                  45

Lys Tyr Ala Ser Gln Ser Ile Ser Gly Ile Pro Ser Arg Phe Ser Gly
     50                  55                  60

Ser Gly Ser Gly Ser Asp Phe Thr Leu Ser Ile Asn Ser Val Glu Pro

```
                65                  70                  75                  80
Glu Asp Val Gly Val Tyr Tyr Cys Gln Asp Gly His Ser Phe Pro Pro
                            85                  90                  95

Thr Phe Gly Gly Gly Thr Lys Leu Glu Ile Lys
            100                 105
```

```
<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Variable
      region of heavy chain of mouse monoclonal antibody
      4B4-1-1

<400> SEQUENCE: 39

Gln Val Gln Leu Gln Gln Pro Gly Ala Glu Leu Val Lys Pro Gly Ala
  1               5                  10                  15

Ser Val Lys Leu Ser Cys Lys Ala Ser Gly Tyr Thr Phe Ser Ser Tyr
                 20                  25                  30

Trp Met His Trp Val Lys Gln Arg Pro Gly Gln Val Leu Glu Trp Ile
             35                  40                  45

Gly Glu Ile Asn Pro Gly Asn Gly His Thr Asn Tyr Asn Glu Lys Phe
         50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Phe Thr Thr Ala Arg Ala Phe Ala Tyr Trp Gly Gln Gly
            100                 105                 110

Thr Leu Val Thr Val Ser Ala
        115

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Variable
      region of light chain of human antibody (X82934)

<400> SEQUENCE: 40

Asp Val Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Arg Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Arg Ser Asn Trp Pro Pro Leu
                 85                  90                  95

Thr Phe Gly Gly Gly Thr Lys Val Glu Ile Lys
            100                 105

<210> SEQ ID NO 41
<211> LENGTH: 119
```

```
<212> TYPE: PRT
<213> ORGANISM: Artificial Sequence
<220> FEATURE:
<223> OTHER INFORMATION: Description of Artificial Sequence: Variable
      region of heavy chain of human antibody (M17750)

<400> SEQUENCE: 41

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Glu Gly
            100                 105                 110

Thr Leu Val Thr Val Ser Ser
        115

<210> SEQ ID NO 42
<211> LENGTH: 415
<212> TYPE: DNA
<213> ORGANISM: Artificial Sequence
<220> FEATURE:
<223> OTHER INFORMATION: Description of Artificial Sequence: Gene coding
      for the variable region of light chain of
      humanized antibody Hz4B4-1

<400> SEQUENCE: 42
actagagctt catcagacag gcaggggaag caagatggat tcacaggccc aggttcttat      60
gttactgctg ctatgggtat ctggtacctg tggggacatt gtgatgaccc agtctccagc     120
cacccagtct gtgtctccag gagaaagagt cacccttttcc tgcagggcca gccagactat    180
tagcgactac ttacactggt atcaacaaaa acctggccag tctccaaggc ttctcatcaa     240
atatgcttcc caatccatct ctgggatccc ctccaggttc agtggcagtg gatcagggtc     300
agatttcact ctcaccatca gcagtgtgga acctgaagat tttggagtgt attactgtca     360
agatggtcac agctttcctc cgacgttcgg tggaggcacc aagctagaaa tcaaa          415

<210> SEQ ID NO 43
<211> LENGTH: 423
<212> TYPE: DNA
<213> ORGANISM: Artificial Sequence
<220> FEATURE:
<223> OTHER INFORMATION: Description of Artificial Sequence: Gene coding
      for variable region of heavy chain of humanized
      antibody Hz4B4-1

<400> SEQUENCE: 43
gccgccacca tgggatggag ctatatcatc ctcttttttgg tagcaacagc tacagatgtc     60
cactcccagg tccaactggt gcagtctggg gctgaagtgg tgaagcctgg ggcttcagtg     120
aagctgtcct gcaaggcttc tggctacacc ttcagcagct actggatgca ctgggtgaag    180
caggcccctg gacaagtcct tgagtggatt ggagagatta tcctggcaa cggtcatact     240 aactacaatg agaagttcaa gagcaaggcc acactgactg tagacaaatc cgcgagcaca    300
```

```
gcctacatgg agctcagcag cctgagatct gaggacacgg cggtctatta ctgtgcaaga    360
tcttttacta cggcacgggc gtttgcttac tggggccaag ggactctggt cactgtctct    420
tca                                                                  423
```

<210> SEQ ID NO 44
<211> LENGTH: 415
<212> TYPE: DNA
<213> ORGANISM: Artificial Sequence
<220> FEATURE:
<223> OTHER INFORMATION: Description of Artificial Sequence: Gene coding
      for variable region of light chain of mouse
      monoclonal antibody 4B4-1-1

<400> SEQUENCE: 44

```
actagagctt catcagacag gcagggggaag caagatggat tcacaggccc aggttcttat    60
gttactgctg ctatgggtat ctggtacctg tggggacatt gtgatgaccc agtctcaagc   120
cacccagtct gtgactccag gagatagagt ctctctttcc tgcagggcca gccagactat   180
tagcgactac ttacactggt atcaacaaaa atcacatgag tctccaaggc ttctcatcaa   240
atatgcttcc caatccatct ctgggatccc ctccaggttc agtggcagtg gatcagggtc   300
agatttcact ctcagtatca acagtgtgga acctgaagat gttggagtgt attactgtca   360
agatggtcac agctttcctc cgacgttcgg tggaggcacc aagctagaaa tcaaa        415
```

<210> SEQ ID NO 45
<211> LENGTH: 423
<212> TYPE: DNA
<213> ORGANISM: Artificial Sequence
<220> FEATURE:
<223> OTHER INFORMATION: Description of Artificial Sequence: Gene coding
      for variable region of heavy chain of mouse
      monoclonal antibody 4B4-1-1

<400> SEQUENCE: 45

```
gccgccacca tgggatggag ctatatcatc ctcttttttgg tagcaacagc tacagatgtc    60
cactcccagg tccaactgca gcagcctggg gctgaactgg tgaagcctgg ggcttcagtg   120
aagctgtcct gcaaggcttc tggctacacc ttcagcagct actggatgca ctgggtgaag   180
cagaggcctg gacaagtcct tgagtggatt ggagagatta tcctggcaa cggtcatact    240 aactacaatg agaagttcaa gagcaaggcc acactgactg tagacaaatc ctccagcaca   300
gcctacatgc aactcagcag cctgacatct gaggactctg cggtctatta ctgtgcaaga   360
tcttttacta cggcacgggc gtttgcttac tggggccaag ggactctggt cactgtctct   420
gca                                                                  423
```

<210> SEQ ID NO 46
<211> LENGTH: 415
<212> TYPE: DNA
<213> ORGANISM: Artificial Sequence
<220> FEATURE:
<223> OTHER INFORMATION: Description of Artificial Sequence: Gene coding
      for variable region of light chain of humanized
      antibody Hz4B4-2

<400> SEQUENCE: 46

```
actagagctt catcagacag gcagggggaag caagatggat tcacaggccc aggttcttat    60
gttactgctg ctatgggtat ctggtacctg tggggacatt gtgatgaccc agtctccacc   120
aaccctttct ctgtctccag gagaaagagt caccctttcc tgcagggcca gccagtccat   180
```

```
tagcgactac ttacactggt atcaacaaaa acctggccag tctccaaggc ttctcatcaa      240
atatgcttcc caatccatct ctgggatccc cgctaggttc agtggcagtg gatcagggac      300
cgatttcact ctcaccatca gcagtctgga acctgaagat tttgctgtgt attactgtca      360
agatggtcac agctttcctc cgacgttcgg tggaggcacc aaggtggaaa tcaaa           415
```

<210> SEQ ID NO 47
<211> LENGTH: 423
<212> TYPE: DNA
<213> ORGANISM: Artificial Sequence
<220> FEATURE:
<223> OTHER INFORMATION: Description of Artificial Sequence: Gene coding
    for variable region of heavy chain of humanized
    antibody Hz4B4-2

<400> SEQUENCE: 47

```
gccgccacca tgggatggag ctatatcatc ctcttttttgg tagcaacagc tacagatgtc      60
cactcccagg tccaactggt gcagtctggg gctgaagtga agaagcctgg ggcttcagtg      120
aaggtgtcct gcaaggcttc tggctacacc ttcagcagct actggatgca ctgggtgcgc      180 caggccctg gacaacgcct tgagtggatg ggagagatta atcctggcaa cggtcatact       240
aactactccc agaagttcca gggacgcgtg acaatcactg tagacaaatc cgcgagcaca      300
gcctacatgg agctcagcag cctgagatct gaggacacgg cggtctatta ctgtgcaaga      360
tcttttacta cggcacgggc gtttgcttac tggggccaag ggactctggt cactgtctct      420
tca                                                                    423
```

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Primer
    Ryu-93

<400> SEQUENCE: 48

```
gaagtcgacc taacactctc ccctgtt                                           27
```

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Primer
    Ryu-101

<400> SEQUENCE: 49

```
cggtcgactc atttacccgg agacag                                            26
```